United States Patent [19]

Marsili et al.

[11] 4,007,169
[45] Feb. 8, 1977

[54] METHOD OF PREPARING DERIVATIVES OF RIFAMYCIN S

[75] Inventors: Leonardo Marsili, Milan; Vittorio Rossetti, Melzo (Milan); Carmine Pasqualucci, Milan, all of Italy

[73] Assignee: Archifar Industrie Chimiche del Trentino S.p.A., Roverto, Italy

[22] Filed: Oct. 16, 1975

[21] Appl. No.: 623,117

[30] Foreign Application Priority Data

Oct. 29, 1974 Italy .................................. 28908/74

[52] U.S. Cl. .......................... 260/239.3 P; 424/244
[51] Int. Cl.² ........................................ C07D 498/08
[58] Field of Search ............................ 260/239.3 P

[56] References Cited

UNITED STATES PATENTS

| | | | |
|---|---|---|---|
| 3,542,765 | 11/1970 | Bickel et al. | 260/239.3 P |
| 3,865,812 | 2/1975 | Cricchio et al. | 260/239.3 P |
| 3,900,465 | 8/1975 | Cricchio et al. | 260/239.3 P |

OTHER PUBLICATIONS

Kump et al., "Helv. Chim. Acta," vol. 56, No. 7, (1973), pp. 2348–2377.
Fieser et al., "J. Am. Chem. Soc.," vol. 57, pp. 1482–1484, (1935).

*Primary Examiner*—Henry R. Jiles
*Assistant Examiner*—Robert T. Bond
*Attorney, Agent, or Firm*—Oblon, Fisher, Spivak, McClelland & Maier

[57] ABSTRACT

Method of preparing 3-amino-Rifamycin S and 3-azido-Rifamycin S and 25-desacetyl derivatives thereof having antibiotic activity. According to such a method, Rifamycin S is dissolved in dipolar aprotic solvent and reacted with sodium azide.

7 Claims, No Drawings

METHOD OF PREPARING DERIVATIVES OF RIFAMYCIN S

The present invention is concerned with a method of preparing derivatives of Rifamycin S and is also concerned with novel derivatives of Rifamycin S.

Well known are the antibiotic properties of Rifamycin S and some derivatives thereof, such as Rifamycin SV and Rifampycin.

Among the derivatives of Rifamycin S, German Patent No. 1,670,377 and Helvetica Chimica Acta, 56, 2368 (1973) disclose the 3-amino derivatives of Rifamycin S, compounds having a high antibacterial property and obtained by direct amination; according to such a method, yields are varying, but particularly low (less than 1%) for the family founder of the products obtained, that is for 3-amino-Rifamycin S. Since the applicants of the present invention deemed that this latter product could as well be a very reactive intermediate for use in the synthesis of novel rifamycins, the applicants have searched for and provided a method enabling the production of 3-amino-Rifamycin S with high yields.

According to such a method, a compound having the formula

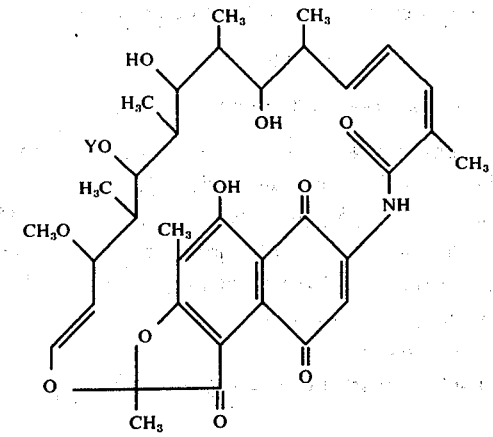

wherein Y is —H or —COCH$_3$, is dissolved in a dipolar aprotic solvent at a temperature ranging between 0° and +100° C, then adding sodium azide and stirring for at least 30 minutes to provide derivatives of Rifamycin S that are isolated according to conventional techniques known in the art.

According to literature ("The Chemistry of the Azido Group" by Saul Patai, Interscience Publishers, 1971, Page 127), benzoquinones provide azidoquinones by azidation, and naphtoquinones provide aminonaphtoquinones. Attempts repeatedly carried out to react Rifamycin S with sodium azide under the above described conditions were unsuccessful. Surprisingly, it was found that using a dipolar aprotic solvent as a solvent, Rifamycin S reacts under not drastic conditions to provide simultaneously three different products, namely 3-amino Rifamycin S, 3-azido Rifamycin S and Rifamycin SV, according to the following scheme:

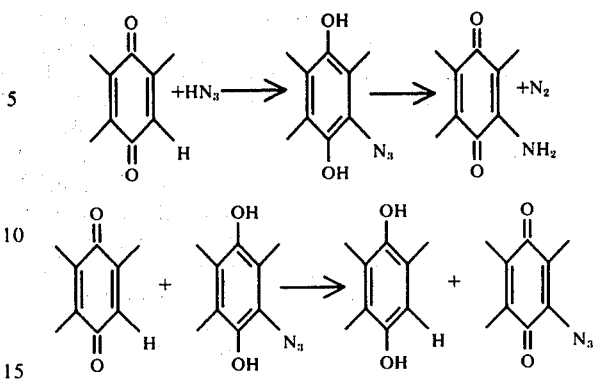

One of these products, namely 3-azido Rifamycin S, is per se a novel product, it is also the subject of the present invention and has higher antibiotic activity than Rifamycin S, in addition to being an interesting product as intermediate in the synthesis of novel derivatives of Rifamycin S.

To summarize, with the method according to the present invention compounds are obtained of the following general formula:

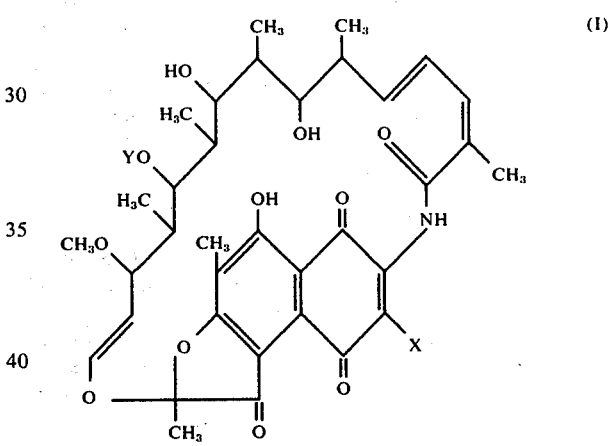

wherein X is —N$_3$ and —NH$_2$, and Y is —H or COCH$_3$.

In order that the features of the present invention be more clearly understood, some examples of the claimed method and product will now be described by unrestrictive way.

In the examples, chromatographies on thin layer have been carried out on silica gel plates (Merck) and the eluting systems have been those hereinafter indicated:

| | | | |
|---|---|---|---|
| Eluent A | = benzene/methanol/ | ethyl acetate | 13:2:2 |
| Eluent B | = benzene/methanol/ | ethyl acetate | 13:4:2 |
| Eluent C | = chloroform/methanol | | 9:1 |

All of the infrared spectra shown in the examples have been carried out in nujol.

EXAMPLE 1

Preparation of 3-azido rifamycin S and 3-amino rifamycin S

Within a 250 ml 4 neck flask, 20 g rifamycin S were dissolved in 60 ml formamide. The solution was heated to 33° C and added with 3.7 g sodium azide in small fractions during 15 minutes. Upon completion of sodium azide addition, the mixture was stirred at 33° C for about 7 hours. The reaction mixture was poured into chloroform, washed with water and then with an aqueous solution of bibasic sodium phosphate. The chloroform phase, washed once with water, was dried on sodium sulphate and then evaporated under vacuum to dryness. The residue obtained (14 g) was separated by chromatography on a column prepared with 1000 g Kieselgel G (Merck). The product was eluted with isopropyl ether containing 3% methanol. The first green coloured eluate was evaporated and crystallized from cyclohexane-carbon tetrachloride.

4.5 g 3-azido rifamycin S were obtained.

Rf(A) = 0.65.

I.R. Spectrum : 3320, 2120, 1735(sh), 1710, 1660, 1615, 1575, 1510(sh), 1420, 1328, 1300, 1250, 1190, 1160, 1095, 1065, 1020(sh), 975, 828, 880, 860 cm$^{-1}$.

After eluting the first fraction, the percentage of methanol in isopropyl ether was increased from 3 to 10%, thus obtaining a second dark red coloured eluate. By solvent evaporation, a residue is obtained which, recrystallized from Xylene, yields 5.5 g 3-amino rifamycin S.

Rf(A) = 0.51.

I.R. Spectrum: 3700, 3500, 1710, 1730, 1645, 1610, 1585, 1510, 1325, 1295, 1258, 1178, 1155, 1125, 1075, 1020, 980, 945, 920, 892, 835, 725cm$^{-1}$.

Column chromatography can be replaced by fractional crystallization from 2-methoxy ethanol, enabling to obtain 3-amino rifamycin S as first precipitate.

EXAMPLE 2

3-amino rifamycin SV 8 g 3-amino rifamycin S were mixed with 40 ml methanol, then brought to ebullition and drop adding to pH 7.8 a solution obtained by dissolving 6.8 g ascorbic acid and 3.2 g sodium carbonate in 50 ml water. Upon addition completion, the product was diluted with a solution of 1.3 g sodium acetate tri-hydrate in 25 ml water, the hot red solution was filtered, diluted with water to 160ml final volume and allowed to rest for 24 hours at 0°–5° C. The product was filtered and dried at 50° C. 7 g sodium salt 3-amino rifamycin SV were obtained.

Rf(B) = 0.11.

Instead of using ascorbic acid, the above described reduction could be carried out by using a salt thereof, or zinc and acetic acid.

EXAMPLE 3

Preparation of 3-amino rifamycin S 45 g rifamycin S were dissolved in 150 ml methyl formamide at room temperature. 5.6 g sodium azide were added, then stirring at room temperature for 15 minutes. The mixture was then heated to 35° C for 60 minutes, diluted with 300 ml methylene chloride and washed with 200 ml water. The aqueous phase contains rifamycin SV, from which rifamycin S was recovered by oxidation with usual oxidizing agents, such as nitrous acid.

On the other hand, the organic phase was further washed with water, dried with sodium sulphate and evaporated.

The residual solid was recristallized from 2-methoxy ethanol, thus obtaining 15 g 3-amino rifamycin S identical to that obtained in Example 1.

EXAMPLE 4

Preparation of 3-amino-25-desacetyl-rifamycin S 4 g 25-desacetyl-rifamycin S were dissolved in 20 ml methyl formamide and added with 0.55 g sodium azide. After 10 hours stirring at room temperature, the solution was added with 100 ml chloroform and washed three times with water. The product was dried on sodium sulphate, concentrated to 15 ml and allowed to crystallize in refrigerator.

1.2 g 3-amino-25-desacetyl-rifamycin S were obtained.

Rf(C) = 0.65.

The same product can be readily obtained by disacetylizing 3-amino-rifamycin S according to techniques known in art.

EXAMPLE 5

Preparation of 3-amino-rifamycin S 50 g rifamycin S were dissolved in 200 ml dimethyl formamide and added with 9 g sodium azide. After 36 hours at a temperature of +5° C, the reaction mixture was treated as in Example 3, to obtain 13 g 3-amino-rifamycin S identical to that described in Example 3.

EXAMPLE 6

Preparation of 3-amino-rifamycin S 14 g rifamycin S were dissolved in 70 ml pyrrolidone and added with 2.6 g sodium azide. The solution was heated at 60° C for 15 min., then at 80° C for further 15 min. The reaction mixture was then treated as in Example 3 to obtain 3.2 g 3-amino-rifamycin S identical to that described in Example 3.

What we claim is:

1. A method of preparing a Rifamycin S having the formula:

wherein X is —N$_3$ or —NH$_2$ and Y is —H or —COCH$_3$, wherein a compound having the formula:

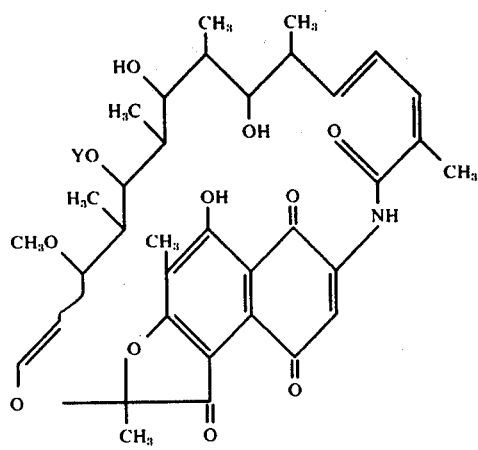

(II)

in which Y is as above defined, is dissolved in a dipolar aprotic solvent at a temperature ranging between 0° and +100° C, adding sodium azide and stirring for at least 30 minutes, a compound of formula I so obtained being recovered from the reaction mass.

2. A method according to claim 1, wherein a compound of Formula I is recovered from the reaction mass by processing said mass with at least one water immiscible solvent selected from the group consisting of methylene chloride, chloroform, ethyl ether, benzene, toluene, and xylene and with water, the compound being then extracted from the solvent used.

3. A method according to claim 2, wherein a compound of formula (I), in which X is —N₃, is separated from that in which X is —NH₂, by fractional crystallization.

4. A method according to claim 1, wherein said dipolar aprotic solvent is selected from the group consisting of methyl acetamide, dimethyl acetamide, methyl formamide, formamide, dimethyl formamide, hexamethyl-phospho-triamide, dimethyl sulphoxide and pyrrolidone.

5. A method according to claim 3, wherein said fractional crystallization is carried out by using 2-methoxyethanol.

6. A Rifamycin S of the formula:

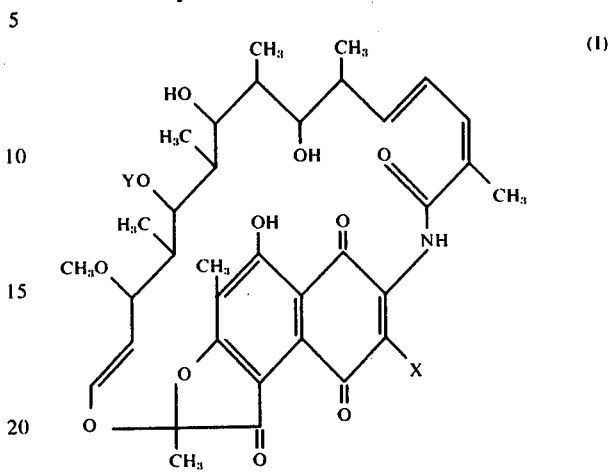

(I)

wherein X is —N₃ and Y is —H or —COCH₃.

7. A Rifamycin S of formula (III) wherein X is —N₃ and Y is H or —COCH₃

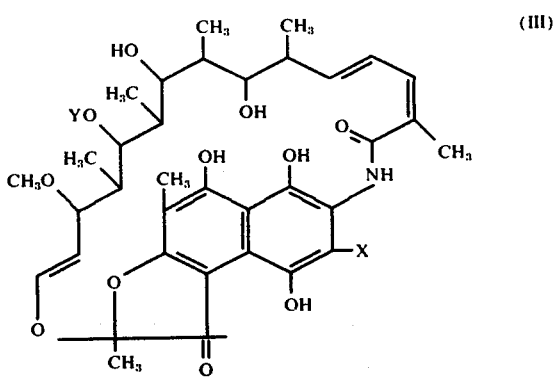

(III)

* * * * *